[12] United States Patent
Fu et al.

(10) Patent No.: US 11,199,533 B2
(45) Date of Patent: Dec. 14, 2021

(54) MICROSCALE WHOLE BLOOD COAGULATION ASSAY PLATFORM (71) Applicant: THE REGENTS OF THE UNIVERSITY OF MICHIGAN, Ann Arbor, MI (US)

(72) Inventors: Jianping Fu, Ann Arbor, MI (US); Kevin R. Ward, Glen Allen, VA (US); Zida Li, Ann Arbor, MI (US); Xiang Li, Ann Arbor, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 544 days.

(21) Appl. No.: 16/079,829

(22) PCT Filed: Feb. 28, 2017

(86) PCT No.: PCT/US2017/019846
§ 371 (c)(1),
(2) Date: Aug. 24, 2018

(87) PCT Pub. No.: WO2017/155736
PCT Pub. Date: Sep. 14, 2017

(65) Prior Publication Data
US 2019/0041380 A1 Feb. 7, 2019

Related U.S. Application Data (60) Provisional application No. 62/304,385, filed on Mar. 7, 2016.

(51) Int. Cl.
G01N 33/49 (2006.01)
G01L 1/18 (2006.01)
G01L 1/22 (2006.01)

(52) U.S. Cl.
CPC ............ *G01N 33/4905* (2013.01); *G01L 1/18* (2013.01); *G01L 1/2287* (2013.01)

(58) Field of Classification Search
CPC ........... C12Q 2527/153; G01N 11/165; G01N 33/4905; B01L 3/5027; G01L 1/18; G01L 1/2287
See application file for complete search history.

(56) References Cited

U.S. PATENT DOCUMENTS 5,293,772 A * 3/1994 Carr, Jr. ............. G01N 33/4905
422/73
6,200,532 B1 3/2001 Wu et al.
(Continued)

OTHER PUBLICATIONS

Li, Zida et al., "A miniaturized hemoretractometer for blood clot retraction testing," small, Jun. 1, 2016 (e-pub), vol. 12 No. 29, pp. 3926-3934. See pp. 3926-3929; and figure 1.
(Continued)

*Primary Examiner* — Dean Kwak
(74) *Attorney, Agent, or Firm* — Marshall, Gerstein & Borun LLP (57) ABSTRACT A blood clot retraction assay device and methods of measuring whole-blood clot retractive forces during coagulation are described. When placed in proximity to a micro-beam, a blood droplet attaches thereto, applying a force to the micro-beam during clot formation. Using Piezoresistive micro-beams or other Piezoresistive components disposed upon such micro-beams, the device measures retractive force of a blood droplet based upon changes in resistance. The sensitivity of such measurements allows use of small quantities of blood for measurement, between 15 microliters and 300 microliters. The device further permits continuous measurement of coagulation, allowing measurement of distinct reaction, contraction development, and fibrinolysis phases for each blood sample.

5 Claims, 7 Drawing Sheets

(56) References Cited

U.S. PATENT DOCUMENTS

| | | | | |
|---|---|---|---|---|
| 8,132,611 | B2* | 3/2012 | Cohn | B82Y 40/00 |
| | | | | 164/46 |
| 8,328,720 | B2* | 12/2012 | Mir | A61B 5/02035 |
| | | | | 600/369 |
| 8,740,818 | B2 | 6/2014 | Walker et al. | |
| 9,213,024 | B2 | 12/2015 | Sniadecki et al. | |
| 2004/0058335 | A1* | 3/2004 | Su | G01N 33/54373 |
| | | | | 435/6.19 |
| 2005/0027184 | A1* | 2/2005 | Saldivar | G01N 33/00 |
| | | | | 600/368 |
| 2010/0015649 | A1* | 1/2010 | Day | G01N 33/49 |
| | | | | 435/13 |
| 2013/0205875 | A1* | 8/2013 | Lal | G01N 29/2437 |
| | | | | 73/54.41 |
| 2015/0017067 | A1 | 1/2015 | Ibbotson et al. | |
| 2015/0056643 | A1* | 2/2015 | Sniadecki | C12M 41/46 |
| | | | | 435/29 |
| 2015/0108010 | A1 | 4/2015 | Ross et al. | |
| 2017/0328883 | A1* | 11/2017 | Gill | G01B 11/16 |

OTHER PUBLICATIONS

International Search Report for Application No. PCT/US2017/019846, dated Jun. 15, 2017.

Extended European Search Report for Application No. 17763750.1, dated Nov. 15, 2019.

Ganter et al., "Coagulation Monitoring: Current Techniques and Clinical Use of Viscoelastic Point-of-Care Coagulation Devices," Anesthesia & Analgesia, 106(5):1336-1375 (2008).

Judith et al., "Micro-Elastometry on Whole Blood Clots using Actuated Surface-Attached Posts (ASAPs)," Lab on a Chip, 15(7):1385-1393 (2015).

Liang et al., "Platelet Retraction Force Measurements Using Flexible Post Force Sensors," Lab on a Chip, 10(8):991-998 (2010).

\* cited by examiner

MICROSCALE WHOLE BLOOD COAGULATION ASSAY PLATFORM

CROSS-REFERENCE TO RELATED APPLICATION

The present application is the US national phase of International Application No. PCT/US2017/019846, filed Feb. 28, 2017, which claims the benefit of the filing date of U.S. Provisional Application No. 62/304,385, filed Mar. 7, 2016, which is hereby incorporated herein by reference in its entirety.

FIELD OF THE DISCLOSURE

This disclosure relates generally to monitoring of blood coagulation and, more specifically, to a system and method for continuous or periodic monitoring of blood to determine its coagulation status, in real time, using a microscale coagulation monitoring platform.

BACKGROUND

Blood coagulation is a critical hemostatic process involving an intricate interplay between cellular (red blood cells, white blood cells, and platelets) and acellular components (plasma proteins) of the blood. Key, N., et al., *Practical hemostasis and thrombosis*. 2009: Wiley Online Library; Tanaka, K. A., N. S. Key, and J. H. Levy, *Blood coagulation: hemostasis and thrombin regulation*. Anesthesia & Analgesia, 2009. 108(5): p. 1433-1446. Blood coagulation is normally initiated when a blood vessel is injured and the connective tissues (particularly collagen) underlying the endothelial lining of the blood vessel are exposed to blood flow, leading to platelet adhesion to connective tissues and their activation and aggregation, forming a plug at the site of vessel injury. Nuyttens, B. P., et al., Platelet adhesion to collagen. Thrombosis research, 2011. 127: p. S26-S29.

Blood coagulation is a critical hemostatic process that must be properly regulated to maintain a delicate balance between bleeding and clotting. Disorders of blood coagulation can expose patients to the risk of either bleeding disorders or thrombotic diseases, such as heart attack, stroke, deep venous thrombosis, or pulmonary embolism. Bennett, J. S., *Platelet-Fibrinogen Interactions*. Annals of the New York Academy of Sciences, 2001. 936(1): p. 340-354. Alternatively, misuse of medicines to slow coagulation for treating thrombotic disorders can place patients at risk for bleeding complications such as internal hemorrhage, excessive bruising, hemorrhagic strokes, etc. Therefore, the ability to rapidly determine the hemostatic profile of a patient is of great importance for providing timely and appropriate therapy in clinical settings such as perioperative hemostatic monitoring, transfusion therapies, thrombotic and hemophilic disease treatments, treatments for multisystem trauma, sepsis, and traumatic brain injury, therapeutic endpoints to anticoagulant medicines, and other acute diseases. Key, N., et al., *Practical hemostasis and thrombosis*. 2009: Wiley Online Library; Bombeli, T. and D. Spahn, *Updates in perioperative coagulation: physiology and management of thromboembolism and haemorrhage*. British journal of anaesthesia, 2004. 93(2): p. 275-287; Aggeler, P. M., *Physiological basis for transfusion therapy in hemorrhagic disorders: a critical review*. Transfusion, 1961. 1(2): p. 71-86.

Coagulation diagnostics using whole blood is very promising for assessing the complexity of the coagulation system and for global measurements of hemostasis. Compared to routine coagulation tests in the clinic (such as prothrombin time or PT, activated partial thromboplastin time or aPTT, and platelet count), whole-blood coagulation tests offer significant advantages of measuring the whole clotting process, starting with fibrin formation and continuing through to clot retraction and fibrinolysis, and allowing the plasmatic coagulation system to interact with blood cells including platelets, red blood cells, and white blood cells, thereby providing useful additional information on platelet function.

Among different whole blood coagulation tests, viscoelastic hemostasis assays including thromboelastography (TEG) and rotational thromboelastometry (ROTEM) have started to gain significant attention in the clinic. McMichael, M. A. and S. A. Smith, *Viscoelastic coagulation testing: technology, applications, and limitations*. Veterinary Clinical Pathology, 2011. 40(2): p. 140-153. In principle, TEG and ROTEM measure the changes in the shear elastic modulus of whole blood upon clotting. For example, TEG consists of a rotating cup and a pin which is connected to a rotation sensor. A blood sample is held in the cup and the pin is submerged in the blood sample during the assay. When the blood starts clotting, its viscoelasticity changes, leading to changes of rotational amplitudes of the pin when following the rotating cup. The rotational amplitude of the pin is recorded by the rotation sensor and reported for analysis of the viscoelasticity change of the blood sample. Such viscoelastic hemostasis assays have been shown to provide critical information on the interactivity of the major phases of clot formation and lysis and on the functional differences between different cellular and acellular components of the blood for differentiating the mechanism(s) related to clotting abnormalities. Despotis, G. J., et al., *Effect of heparin on whole blood activated partial thromoplastin time using a portable, whole blood coagulation monitor*. Critical Care Medicine, 1995. 23(10): p. 1674-79.

Besides viscoelastic hemostasis assays, whole-blood clot retraction assays using devices such as Hemodyne Hemostasis Analysis System (the HAS™ system was previously produced by Hemodyne, Inc.) also provide important information on blood coagulation function by reporting on clot elastic modulus and platelet contractile force (or clot retraction force). In the HAS™ system, whole blood samples are confined between two plates (either flat-flat or cone-cone surfaces), with the top plate attached to a strain-gage transducer. Clotting of blood results in a downward force pulling the top plate (or the clot retraction force), which is directly measured in real time by the strain-gage transducer. Using the HAS™ system, clot retraction force has been shown to be sensitive to platelet number and metabolic status, glycoprotein IIB/IIIa status, and the presence of antithrombin activities. Carr Jr, M. E., *Development of platelet contractile force as a research and clinical measure of platelet function*. Cell biochemistry and biophysics, 2003. 38 (1): p. 55-78. Importantly, clinical applications of the HAS™ system have demonstrated promising applications of such whole blood clot retraction assays for rapid assessment of global hemostasis and the response to a variety of procoagulant and anticoagulant medications. Krishnaswarmi, A., et al., *Patients with coronary artery disease who present with chest pain have significantly elevated platelet contractile force*. Thromb Haemostasis, 1999. 82(suppl. 1): p. 162; Greilich, P. E., et al., *Reductions in platelet force development by cardiopulmonary bypass are associated with hemorrhage*. Anesthesia & Analgesia, 1995. 80(3): p. 459-465; Carr, M., et al., *Batroxobin-induced clots exhibit delayed and reduced platelet contractile force in some patients with clotting*

*factor deficiencies.* Journal of Thrombosis and Haemostasis, 2003. 1(2): p. 243-249; Carr, M., et al. *Anticoagulant and antiplatelet activities of heparin and low-molecular-weight derivatives.* in Blood. 1993. Wb Saunders Co Independence Square West Curtis Center, Ste 300, Philadelphia, Pa. 19106-3399; Carr, M., et al. *Dermatan sulfate suppresses platelet force as it prolongs the APTT.* in Blood. 1996. Wb Saunders Co Independence Square West Curtis Center, Ste 300, Philadelphia, Pa. 19106-3399; McCardell, K., S. Carr, and M. Carr. *Aprotinin augments protamine sulfate reversal of heparin antiplatelet effects.* in Journal of Investigative Medicine. 1996. Slack Inc 6900 Grove Rd, Thorofare, N.J. 08086.

Despite the clinical values that the existing whole blood coagulation tests (including TEG, ROTEM, and HAS™) have demonstrated through initial applications, such systems still have significant limitations in terms of costly expense to make and repair, limited sample throughput, large footprint, excessive sample size (>0.3 mL) that can be problematic for repetitive assays on pediatric patients, inter-assay variability, and significant user interventions, rendering them suboptimal or unsuitable for point-of-care applications. Furthermore, these limitations associated with the existing whole blood coagulation tests make it difficult for multiplexed blood assays to define specific coagulation disorders.

Some conventional blood coagulation assay approaches utilize the Piezoelectric effect to stimulate and measure resonance of a blood sample. However, this crude approach does not directly measure the contractive forces during coagulation and requires power regulation to stimulate the blood sample before determining the sample's response. When a Piezoelectric material is deformed under an external pressure or force, such deformation of the material induces an accumulation of electric charge within the material, resulting in a change of electric potential (i.e., voltage) within the material. Conversely, when such Piezoelectric material is applied with an external voltage, it will deform. This is known as the Piezoelectric effect and has known uses in micromechanical motors and voltage measurement.

SUMMARY OF THE DISCLOSURE

Suitable point-of-care coagulation devices that are simple, inexpensive, quick, high throughput, and can be widely available, may be fabricated using functional soft materials to develop a miniaturized clot retraction assay device termed mHemoRetractoMeter (mHRM). In a mHRM of the present disclosure, two doubly-clamped mechanical strain sensing beams made with soft elastomer polydimethylsiloxane (PDMS) are utilized for holding prescribed minute amounts of bloods samples while simultaneously measuring clot retraction force during blood clotting. Different major phases of clot formation and extraction of key blood clotting parameters can be analyzed using kinetic curves of clot retraction force obtained using the mHRM.

Unlike the Piezoelectric effect employed by various conventional blood coagulation assay approaches, the mHRM of the present disclosure employs Piezoresistive effect. The Piezoresistive effect is related to a change in the electrical resistivity of a material when it is deformed under an external pressure or force. The Piezoresistive effect is completely different from the Piezoelectric effect, as this change in resistivity does not involve electric potential. In addition, applying an external voltage to a Piezoresistive material does not cause the material to deform. Using the Piezoresistive effect allows more detailed measurements of changes in the contractive forces that exist during blood coagulation.

DETAILED DESCRIPTION OF THE PREFERRED EMBODIMENTS

A microscale clot retraction assay device of a first embodiment of the present disclosure, also referred to herein as a mHemoRetractoMeter (mHRM) 10, is illustrated in FIGS. 1-5C. The mHRM 10 of this first embodiment features two opposing micro-beams 12, 14. The micro-beams 12, 14 are made of a deformable material that allows them to bend somewhat when an external force is applied. By way of example only, these micro-beams 12, 14 may each have a length of 2 cm, a width of 2 mm, and a thickness of 2 mm. Each of the micro-beams 12, 14 includes a sample platform 16, 18 defining a plateau to support a droplet of blood. Each sample platform 16, 18 is provided on a protrusion 20, 22, illustrated in FIG. 1 as a rectangular projection of, and extending perpendicular to, the respective micro-beam 12, 14 in a direction toward the opposing micro-beam 14, 12. In preferred embodiments, the micro-beams 12, 14 and protrusions 20, 22 are made of soft elastomers to allow plastic deformation in response to applied force from a sample. Such soft elastomer may be polydimethylsiloxane (PDMS), which has advantageous properties relative to displacement in response to an external force load. By using PDMS components, the mHRM 10 is able to achieve a high degree of sensitivity in measuring contractive force of a sample based upon displacement of the micro-beams 12, 14.

The protrusions 20, 22 may be provided with indicia in the form of graduations, such as alternating dashes (-) and crosses (+), to aid in optical detection and measurement of deflection of each of the micro-beams 12, 14. Such optical detection and measurement are described below with respect to FIGS. 5A-C.

In use, a droplet of blood B having a volume as little as about 15 µL is deposited (such as by using a pipette) between the sample platforms 16, 18. The volume of the droplet of blood B is preferably between 15 µL and 300 µL to ensure accurate measurements. The micro-beams 12, 14 are spaced apart from one another such that when a droplet of blood that has not yet significantly coagulated is so deposited on the sample platforms 16, 18, the micro-beams 12, 14 are not in a deflected condition.

Figure 1:
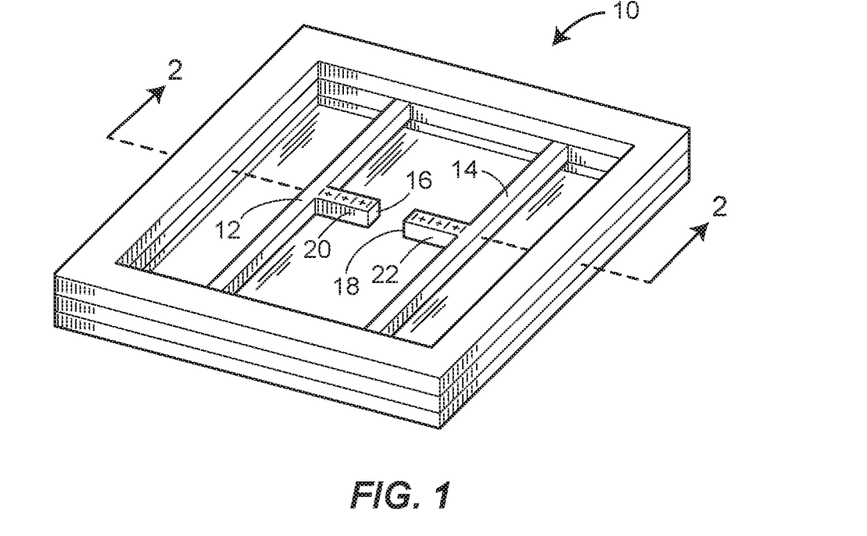
FIG. 1 is a perspective view of a clot retraction assay device of a first embodiment of the present disclosure.
Figure 2:
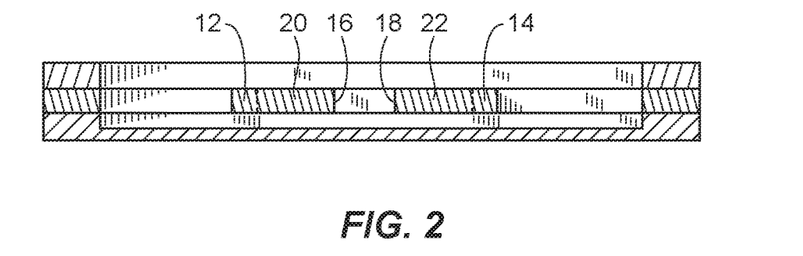
FIG. 2 is a cross-sectional view, taken along lines 2-2 of FIG. 1, of the clot retraction assay device of the first embodiment of the present disclosure.
Figure 3:
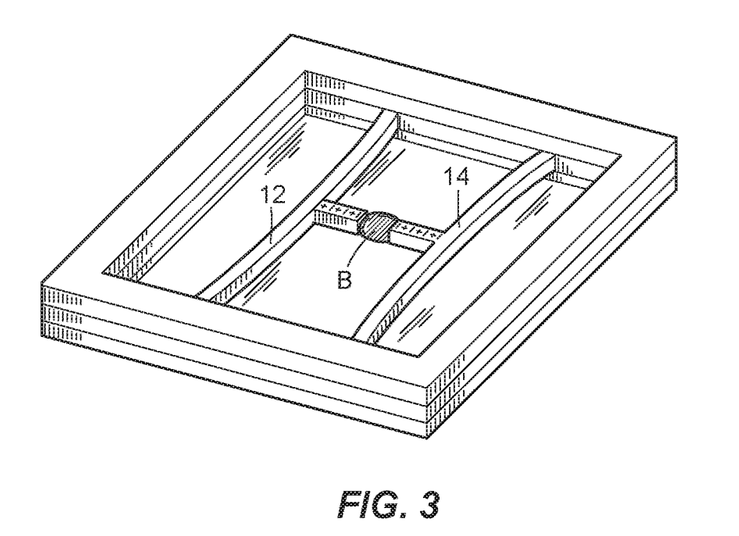
FIG. 3 is a perspective view of the clot retraction assay device illustrated in FIG. 1, with beams of the device deflected toward one another in response to coagulation of a droplet of blood provided between two sample platforms of the clot retraction assay device.
Figure 4:
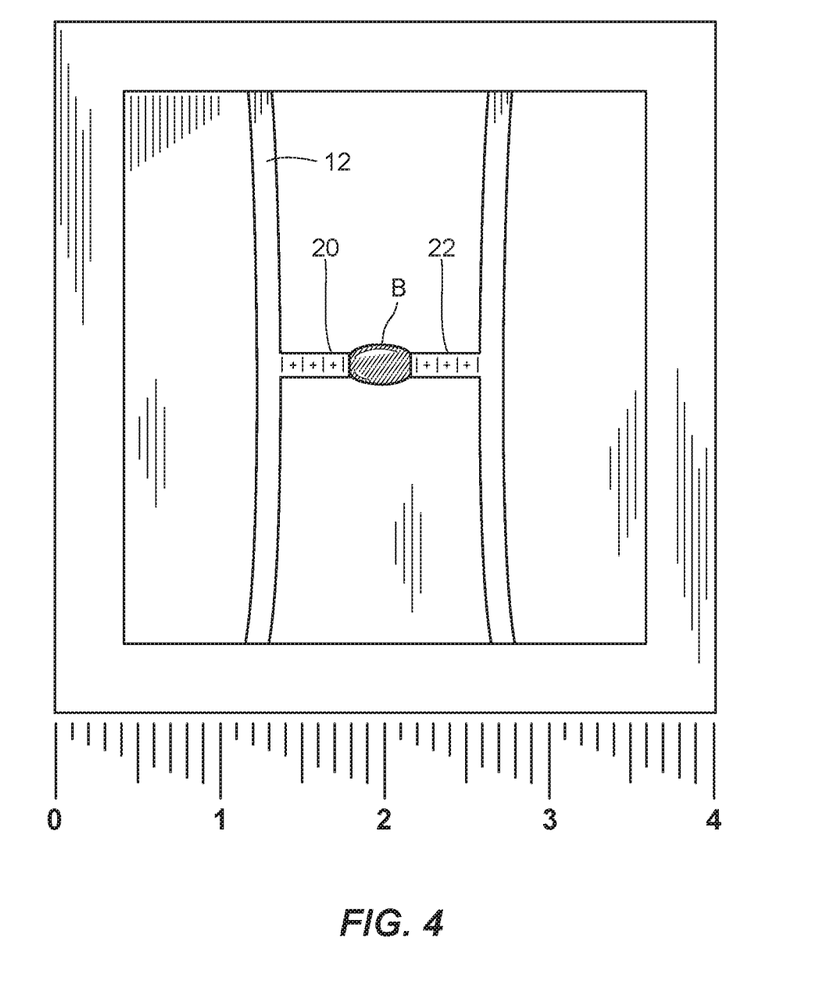
FIG. 4 is a plane view of the clot retraction assay device illustrated in FIG. 3, with graduation markings provided to aid in measuring deflection of the beams in response to coagulation of the droplet of blood provided between the two sample platforms of the clot retraction assay device.
Figure 5A:
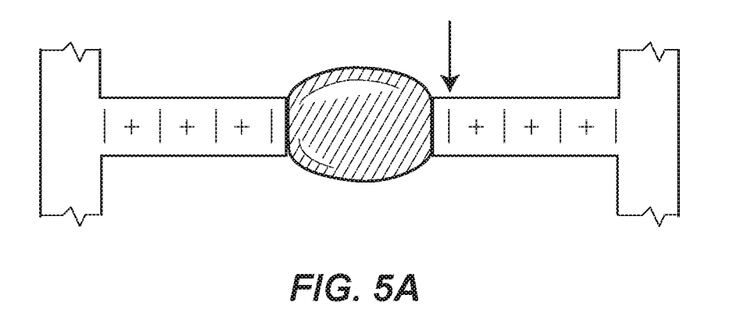
FIG. 5A is an enlarged view, broken away, of the two sample platforms of the clot retraction assay device illustrated in FIG. 3, showing the droplet of blood in a first phase of coagulation, prior to measurable deflection of the beams of the clot retraction assay device.
Figure 5B:
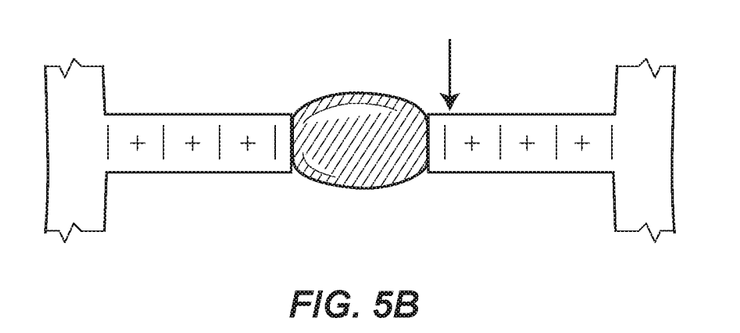
FIG. 5B is an enlarged view, broken away, of the two sample platforms of the clot retraction assay device illustrated in FIG. 3, showing the droplet of blood in a second phase of coagulation, and illustrating some measurable deflection of the beams of the clot retraction assay device as a result of the progression of coagulation of the droplet of blood.
Figure 5C:
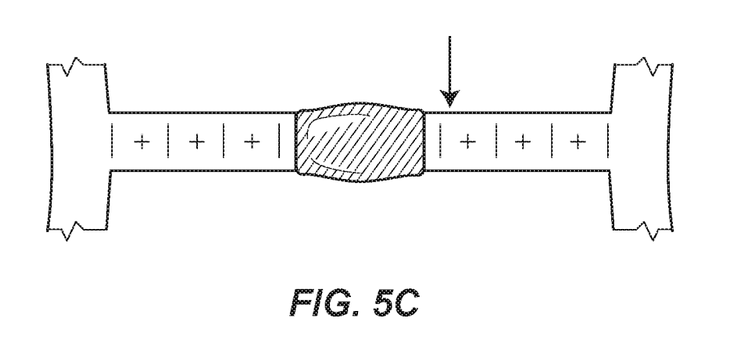
FIG. 5C is an enlarged view, broken away, of the two sample platforms of the clot retraction assay device illustrated in FIG. 3, showing the droplet of blood in a third phase of coagulation, and illustrating further measurable deflection of the beams of the clot retraction assay device beyond that illustrated in FIG. 5B as a result of the further progression of coagulation of the droplet of blood.

Upon platelet activation, the droplet of blood begins to clot, as discussed further below. The clot will contract, exerting a force on each of the micro-beams 12, 14 in the direction toward the opposing micro-beam 14, 12. This can be appreciated with reference to FIGS. 3 through 5C, which illustrate the micro-beams 12, 14 deflecting toward one another as clotting of the droplet of blood B progresses. To measure blood coagulation using the mHRM 10, the extent of micro-beam deflection is measured. As illustrated in FIG. 3, the contraction of droplet of blood B during coagulation exerts a force upon each of micro-beams 12 and 14 that pulls the beams together. The contractive force the droplet of blood B exerts is communicated to the micro-beams through the protrusions 20 and 22 to which the droplet of blood B adheres at the sample platforms 16 and 18, respectively. As illustrated in FIG. 4, the contracting droplet of blood B pulls the protrusions 20 and 22 together, causing the micro-beams 12 and 14 to bend toward the droplet of blood B. FIGS. 5A-C illustrate this process over time. The stationary arrow in each figure is provided to indicate displacement of the micro-beam 14 caused during coagulation. The droplet of blood B is initially placed between the sample platforms 16 and 18 at FIG. 5A, at which point the micro-beams 12 and 14 are not significantly deformed. As coagulation begins and the droplet of blood B exerts a force on the micro-beams 12 and 14 in FIG. 5B, a small deformation of micro-beam 14 is seen by the displacement of the protrusion 22 (relative to the stationary arrow). After a longer period of time, the contractive force exerted by the droplet of blood B causes a greater deformation of the micro-beams 12 and 14, as illustrated in FIG. 5C by the further displacement of the protrusion 22 (relative to the stationary arrow). The indicia provided upon the protrusions 20, 22 aid in observation of the displacement caused by the contractive force exerted by the droplet of blood B.

In some embodiments, a camera may record time-lapse images of the mHRM 10 to determine displacement by comparison of the indicia upon the protrusions 20, 22 over time. By using indicia of known characteristics (e.g., distance between gradations), an observer may calculate the displacement of the protrusions 20, 22 at various times. Such displacement corresponds to the force exerted by the droplet of blood B. It should be understood that the relationship between such displacement and force depends upon the specific configuration of the components of the mHRM, including the dimensions and composition of the micro-beams 12, 14. The relationship between displacement and force may likewise depend upon the temperature of the components. Therefore, the mHRM 10 may include components to measures or control temperature in some embodiments. In further embodiments, an attachment device may be used to securely connect the camera to the mHRM 10 for analysis, which may be of particular use when the camera is easily movable. For example, an attachment device (not shown) may be secured to a mobile computing device (such as a smart phone) having a camera to allow the camera to be used for analysis. In some such embodiments, the attachment device may be incorporated into or may form a part of the mHRM 10. Similarly, the mHRM 10 may be divided into a disposable cartridge portion and a receiver portion containing a camera, ohmmeter, multimeter, or other measurement devices, as described further below.

Notably, the blood coagulation measurement protocol using the mHRM 10 is achieved without pre-functionalization of the device surface, such as through the use of adhesive proteins such as collagen, fibronectin, or other tissue factors. Such protein or lipid-based functionalization requires low-temperature storage of coagulation assay test devices, limiting their potential use for point-of-care applications in resource-limited settings. By utilizing the non-specific adhesion between whole blood and the plateau or surface of the sample platforms 16, 18 of the protrusions 20, 22, protein or lipid-based functionalization is not necessary. Moreover, surface tension between the droplet of blood and the sample platforms 16, 18 minimizes the surface area of the blood sample required for accurate coagulation measurements, resulting in a repeatable clot shape. This aids in increased accuracy of measurements to establish reliable control data, which facilitates the identification of variations from expected coagulation rates for a given test sample. The shape of this clot may form the basis for a new metric or clotting vital sign.

While indicia, such as the graduations described above, may be provided on the protrusions 20, 22 to facilitate optical measurement of micro-beam deflection using a microscope of micro-beam deflection, electrical measurement is more reliable and desirable for point-of-care applications. Thus, the device may be further improved by means of additional features to facilitate electrical measurement of micro-beam deflection. Such electronic measurement may be facilitated by inclusion of conductive carbon black nanoparticles in PDMS components of the mHRM, particularly carbon black nanoparticles having an average size of approximately 50 nm. By percolating PDMS with conductive carbon black nanoparticles and mixing, the carbon black nanoparticles form dense aggregates with PDMS, which renders the carbon-PDMS composite (CPDMS) conductive. For example, at 22% (wt %) carbon black concentration, the CPDMS has an electrical resistivity of $0.2\Omega\cdot m$ in the absence of an external force. To be effective for measurement, the CPDMS should be between 10% and 26% (preferably between 18% and 26%) carbon by weight. Weight ratios below 18% result in limited conductivity (with weight ratios below 10% having particularly limited conductivity), while weight ratios above 26% prove difficult for mixing. In some embodiments, carbon nanotubes (such as multi-walled carbon nanotubes) may be mixed into the PDMS to produce a Piezoresistive CPDMS composite material. Although the discussion herein refers to measurement of changes of resistance in CPDMS composite materials, it should be understood that any soft Piezoresistive material may be substituted. Thus, other conductive polymers that contain nanoscale inclusions of conductive materials (e.g., carbon nanotubes, graphene, or silver particles) may be used as an alternative to the CPDMS composite materials in the embodiments described herein. For example, a thin film of carbon nanotubes may be used as the Piezoresistive material.

To use the CPDMS or other Piezoresistive material for measuring coagulation based upon contractive force, one or more Piezoresistive components (such as CPDMS components) may be included within the mHRM. In particularly advantageous embodiments, the CPDMS components may comprise or be attached to one or more micro-beams (such as the micro-beams 12, 14), so that the CPDMS components are subjected to forces exerted by blood samples. The CPDMS components deform under external force load (such as force exerted by a blood sample during clot formation), and the changing gap size between carbon nanoparticles changes the resistance of the CPDMS components. This change in resistance can be measured using known means (e.g., by a digital or analog ohmmeter or multimeter). The measured change in resistance corresponds to the deformation of the CPDMS components, which further corresponds to the force exerted upon such components. Thus, the measured change in resistance of the one or more CPDMS components may be used to determine the coagulation of a blood sample. It should be appreciated that the relationship between the force exerted by the blood sample and the measured change in resistance of a CPDMS component will depend upon the specific configuration of the mHRM device, including the dimensions and composition of the CPDMS component.

For any particular configuration of an mHRM (such as those embodiments described herein which can measure coagulation in multiple dimensions), the Piezoresistivity of CPDMS can be quantified in order to calibrate the mHRM. As discussed above, the coagulation of a blood sample adhering to a portion of a micro-beam causes deformation of the micro-beam. If the micro-beam is made of CPDMS, such deformation will result in a change to the resistance across the micro-beam. Similarly, if a CPDMS layer is attached to the micro-beam (e.g., by deposition on the micro-beam surface or as a layer within the micro-beam), the CPDMS layer will deform along with the micro-beam, and such deformation will likewise result in a change to the resistance across the CPDMS layer. In either case, the change in resistance can be measured using known means of measuring resistance across the CPDMS component, viz. the CPDMS micro-beam or CPDMS layer. For example, measurements may be taken at a plurality of times using a multimeter or ohmmeter contacting portions of one or more CPDMS components. Alternatively, the mHRM (or a device to which it is connected) may include a dedicated Wheatstone bridge circuit and processing component to measure resistance across a portion of one or more CPDMS components.

The particular design and composition of the CPDMS components affect the resistance of the components. In addition to the geometry of the CPDMS components (e.g., length, cross-sectional area, cross-sectional shape), the specific composition of the CPDMS material (e.g., type and amount of carbon added) also changes the resistance of the CPDMS components. Temperature also has an effect on the resistivity of the CPDMS material. The locations of connections to the resistance-measuring means will also affect the measurement. To accurately measure the force exerted by a blood sample, therefore, the mHRM must be calibrated based upon the particular CPDMS components used therein. Such calibration may be performed by calculating resistance from known characteristics of the component (e.g., resistivity of the particular CPDMS composite material used, length of the component, and cross-sectional area and shape of the component) or may be performed using measurements. Similar CPDMS components may be measured by application of known forces to the components, either in a laboratory testing configuration or in situ within an mHRM device. For example, a force probe may be attached to a micropositioner device, which force probe may then be used to apply various magnitudes of force to the CPDMS component to be tested. The resistance of the CPDMS component being tested may be recorded for each of a plurality of forces thus applied. In embodiments in which the CPDMS component is attached to a micro-beam, the entire micro-beam with the CPDMS component should be tested to accurately determine the relationship between the force applied to the micro-beam and the change in resistance of the CPDMS component. This is further described below with respect to the exemplary embodiment of FIGS. 10-12.

Figure 6:
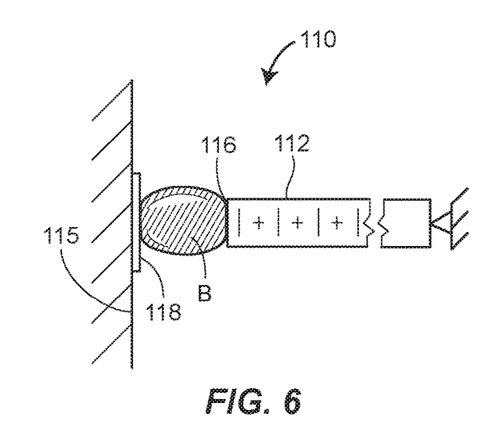
FIG. 6 is an enlarged, semi-schematic view of a portion of a clot retraction assay device in accordance with a second embodiment of the present disclosure, wherein a droplet of blood is received between a fixed wall (indicated schematically by a ground symbol) and a beam (much of which is broken away) running perpendicular to, but when in a non-deflected (i.e. non-stretched) rest or nominal condition, spaced away from the fixed wall a distance coinciding or substantially coinciding with a nominal diameter of a droplet of blood that has not yet experienced significant coagulation.

Turning to FIG. 6A, a portion of a second embodiment of the mHRM 110 is illustrated. In this version, a single micro-beam 112 is oriented perpendicularly to a fixed plane 115, schematically illustrated by a ground symbol. The fixed plane may or may not comprise a conducting (or semi-conducting) material. The micro-beam 112 is initially spaced from the fixed plane 115 such that when a droplet of blood B that has not yet significantly coagulated is deposited on sample platform 116, the micro-beam 112 is not in a deflected condition. According to this embodiment, the fixed plane 115 does not deflect. To facilitate localization of the droplet of blood, the fixed plane 115 may include a circular depression or raised plateau 118, but this does not deflect. Unlike the deflection of the micro-beams 12, 14 of the first embodiment, which was deflection in a plane normal to the longitudinal axis of the micro-beams 12, 14, the deflection of the micro-beam 112 due to progression of coagulation of the droplet of blood B is in the form of stretching of the micro-beam 112 along the longitudinal axis, so that the sample platform 116 moves closer to the raised plateau 118. The micro-beam 112 may be provided with indicia, such as graduations, to facilitate optical measurement of the deflection of the beam due to progression of coagulation of the droplet of blood B.

Alternatively, the micro-beam 112 may comprise a Piezoresistive material, such as CPDMS or other Piezoresistive materials described herein. In such embodiments, the resistance of the micro-beam 112 (or a portion thereof) may be measured, as described elsewhere herein. For example, an ohmmeter may be connected to portions of the micro-beam 112 near its connection to the fixed plane 115 and its sample platform 116. As an alternative example, two points along the length of the micro-beam 112 between the fixed plane 115 and the sample platform 116 may be electrically connected (by electrodes, wires, etc.) to the ohmmeter. Wherever the measurement points connecting the micro-beam 112 to the ohmmeter are located, the ohmmeter may be used to measure the change in resistance as the micro-beam 112 deforms in response to the contractive force of the droplet of blood B. Such measured changes in resistance may be used to calculate or otherwise determine the contractive force exerted by the droplet of blood B. For example, a lookup table may be used to determine the contractive force based upon previously performed experimental measurements and/or calculations. The contractive force thus determined may then be used for further analysis of the coagulation of the droplet of blood B, as described elsewhere herein.

Figure 7A:
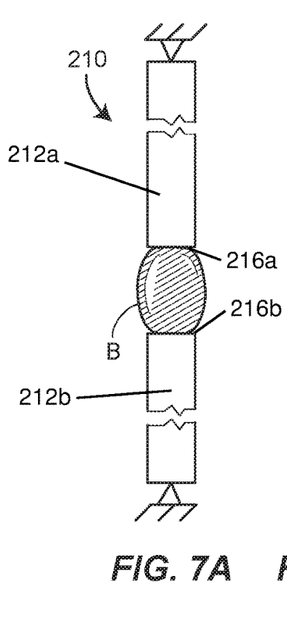
FIG. 7A is an enlarged view of a portion of a clot retraction assay device in accordance with a third embodiment of the present disclosure, featuring two elongate beams positioned coaxially and, in a non-deflected (i.e. non-stretched) rest or nominal condition, spaced away from one another a distance coinciding or substantially coinciding with a nominal diameter of a droplet of blood that has not yet experienced significant coagulation, with a droplet of blood received between the two elongate beams.
Figure 7B:
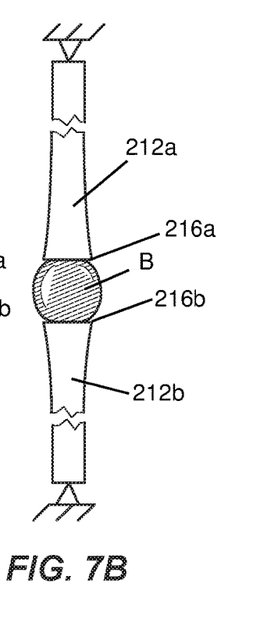
FIG. 7B is an enlarged view of the portion of the clot retraction assay device illustrated in FIG. 7A, showing the two beams stretched toward one another as a result of the progression of coagulation of the droplet of blood.

Turning to FIGS. 7A and 7B, a portion of a third embodiment of the mHRM 210 is illustrated. In this embodiment, a pair of longitudinally coaxial micro-beams 212a and 212b are provided, and a droplet of blood B is placed between the micro-beams 212a, 212b. The micro-beams 212a and 212b are initially spaced apart from one another such that when a droplet of blood B that has not yet significantly coagulated is deposited between the micro-beams 212a, 212b, neither of the micro-beams 212a, 212b is in a deflected condition. Each of the micro-beams 212a, 212b is fixed at an end opposite of the blood sample receiving end or sample platform 216a, 216b of the respective micro-beam, as indicated schematically in FIGS. 7A, 7B by ground symbols. The deflection of the micro-beams 212a, 212b due to progression of coagulation of the droplet of blood B is in the form of stretching of the micro-beams 212a, 212b along each of their longitudinal axis, so that the sample platforms 216a, 216b of the micro-beams 212a, 212b move closer to one another, as illustrated by comparing FIG. 7B to FIG. 7A. Optical and/or Piezoresistive methodologies described herein may be employed to measure the deflection of the micro-beams 212a, 212b and assess the rate and/or phase of coagulation of the droplet of blood B.

Figure 8A:
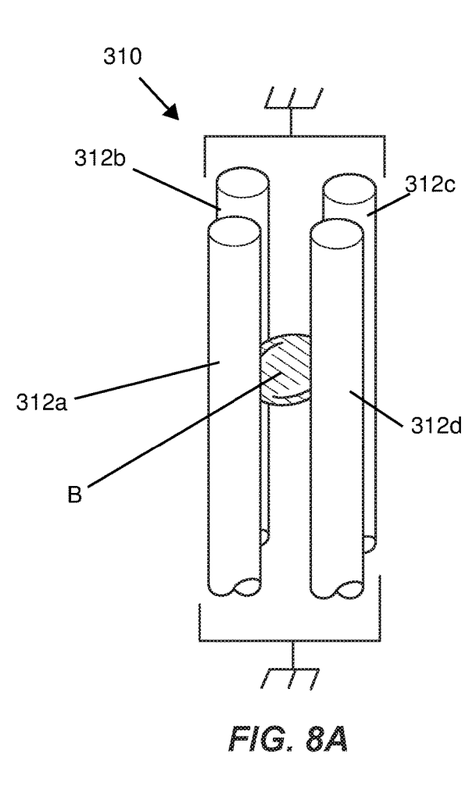
FIG. 8A is an enlarged perspective view of a portion of a clot retraction assay device in accordance with a fourth embodiment of the present disclosure, featuring four elongate beams positioned parallel to one another and spaced from one another in a non-deflected condition such that a droplet of blood that has not yet experienced significant coagulation, when suspended between the four elongate beams, is in contact with each of the four elongate beams, with a droplet of blood received between the four elongate beams.
Figure 8B:
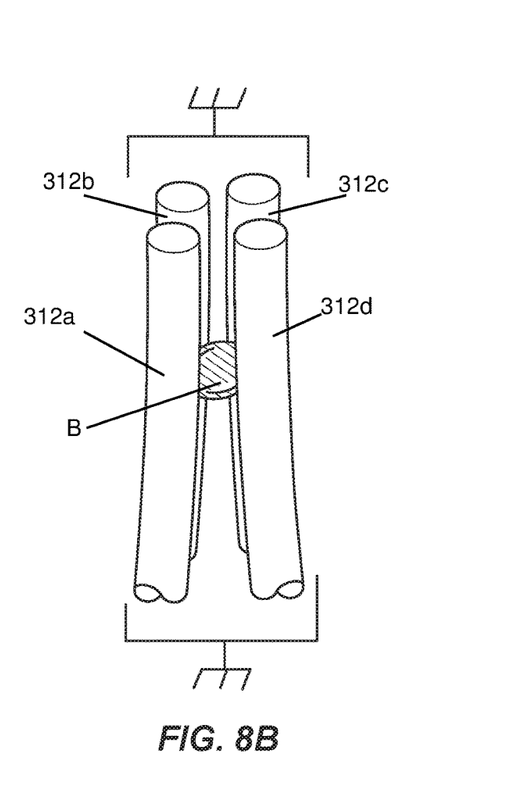
FIG. 8B is an enlarged perspective view of the portion of the clot retraction assay device illustrated in FIG. 8A, showing the two beams deflected toward one another as a result of the progression of coagulation of the droplet of blood.

A portion of a fourth embodiment of the mHRM 310 is illustrated in FIGS. 8A, 8B. In this embodiment, four micro-beams 312a, 312b, 312c, 312d are arranged in parallel, with a droplet of blood B disposed in contact with a platform, preferably located at a longitudinal mid-point, of each of the four micro-beams 312a, 312b, 312c, 312d. The micro-beams 312a, 312b, 312c, 312d are initially spaced apart from one another such that when a droplet of blood B that has not yet significantly coagulated is deposited between the micro-beams 312a, 312b, 312c, 312d, none of the micro-beams 312a, 312b, 312c, 312d is in a deflected condition. Each of the micro-beams 312a, 312b, 312c, 312d is fixed at both ends, as indicated schematically in FIGS. 8A, 8B by ground symbols. The deflection of the micro-beams 312a, 312b, 312c, 312d due to progression of coagulation of the droplet of blood B is in the form of bending of the micro-beams 312a, 312b, 312c, 312d toward one another, so that sample platforms (not shown) of the micro-beams 312a, 312b, 312c, 312d where the droplet of blood B contacts each of the micro-beams 312a, 312b, 312c, 312d move closer to one another, as illustrated by comparing FIG. 8B to FIG. 8A. As in the previous embodiments, optical and/or Piezoresistive methodologies described herein may be employed to measure the deflection of the micro-beams 312a, 312b, 312c, 312d and assess the rate and/or phase of coagulation of the droplet of blood B. An advantage of this approach is the clot formation and characteristics can be measured in multiple dimensions and, therefore, may be more indicative of how native clot formation occurs and interacts with blood vessel surfaces.

Figure 9:
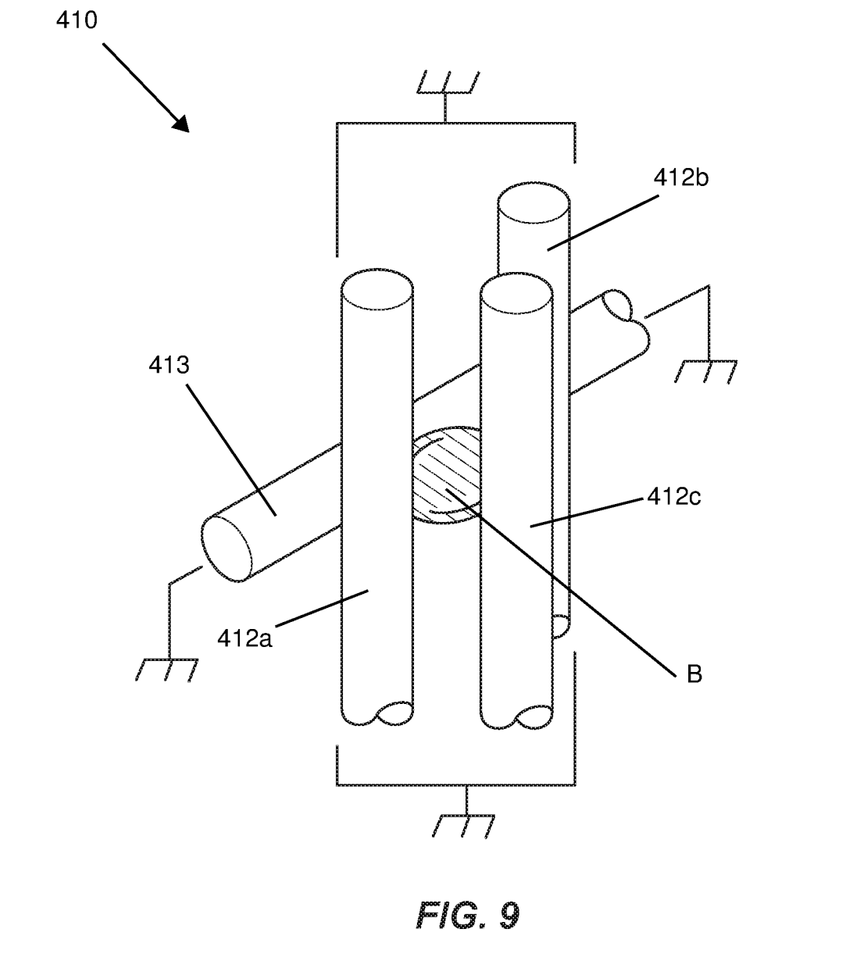
FIG. 9 is an enlarged perspective view of a portion of a clot retraction assay device in accordance with a fifth embodiment of the present disclosure, featuring four elongate beams, three of which are positioned parallel to one another and spaced from one another in a non-deflected condition such that a droplet of blood that has not yet experienced significant coagulation, when suspended between the three elongate beams, is in contact with each of the three elongate beams, and is in further contact with a fourth elongate beam extending perpendicularly to the three elongate beams, with a droplet of blood received between the four elongate beams.

FIG. 9 illustrates a portion of a fifth embodiment of a mHRM 410, which is a variation of the fourth embodiment or a hybrid of the first and fourth embodiments. According to this fifth embodiment, three micro-beams 412a, 412b, 412c are arranged in parallel to one another, and a fourth micro-beam 413 is disposed perpendicularly to the other three micro-beams 412a, 412b, 412c. All four of the micro-beams 412a, 412b, 412c, 413 are fixed at both ends, as indicated schematically in FIG. 9 by ground symbols. The micro-beams 412a, 412b, 412c, 413 are initially spaced apart from one another such that when a droplet of blood B that has not yet significantly coagulated is deposited between the micro-beams 412a, 412b, 412c, 413, none of the micro-beams 412a, 412b, 412c, 413 is in a deflected condition. The deflection of the micro-beams 412a, 412b, 412c, 413 due to progression of coagulation of the droplet of blood B is in the form of bending of the micro-beams 412a, 412b, 412c, 413 toward one another, so that sample platforms (not shown) of the micro-beams 412a, 412b, 412c, 413 where the droplet of blood B contacts each of the micro-beams 412a, 412b, 412c, 413 move closer to one another. As in the previous embodiments, optical and/or Piezoresistive methodologies described herein may be employed to measure the deflection of the micro-beams 412a, 412b, 412c, 413 and assess the rate and/or phase of coagulation of the droplet of blood B.

Additionally, the orientation of the micro-beams 412a, 412b, 412c, and 413 along a plurality of axes facilitates measurement of clot formation in multiple dimensions. As illustrated, the primary axes of micro-beams 412a, 412b, 412c are substantially parallel to one another and orthogonal to the primary axis of micro-beam 413. Thus, the retractive forces of the droplet of blood B may be measured in at least two dimensions perpendicular to these primary axes. The total clot retraction force may be determined based upon the force components in each of a plurality of directions. Additional embodiments may include micro-beams arranged to measure contractive force in any number of dimensions, directions, or points. In such additional embodiments, the micro-beams may be orthogonal or non-orthogonal, and any number of micro-beams may be used to measure the contractive forces in a plurality of directions. By such configuration of a plurality of micro-beams, the regularity or irregularity of the clot may be measured. For example, a clot may be determined to be substantially spherical based upon approximately equivalent forces measured in a plurality of directions, or a clot may be determined to have substantially greater contractive forces in some directions than in others. Additionally, the shapes of clots may be determined based upon such multidimensional measurements. This may be computed from determined forces in each of a plurality of directions, or it may be determined by computing the deformation distances of each of the plurality of micro-beams in each of the directions. Both force and deformation may be determined based upon measurements of resistance across the Piezoresistive components, which may include the micro-beams.

In further embodiments, a multidimensional profile of a clot may be constructed based upon measured contractive forces in a plurality of dimensions. Such a multidimensional profile may indicate the shape or strength of the clot in each dimension at one or more times following the time clotting is induced. For example, the multidimensional profile may include measurements of contractive forces exerted by the droplet of blood B during clotting at regular time intervals (e.g., every quarter-second, every second, etc.) in each of a plurality of directions (e.g., three orthogonal directions, five non-orthogonal directions, etc.). In yet further embodiments, a four-dimensional model of the clot in three-dimensional space over time may be generated based upon, or as part of, the multidimensional model.

Figure 10:
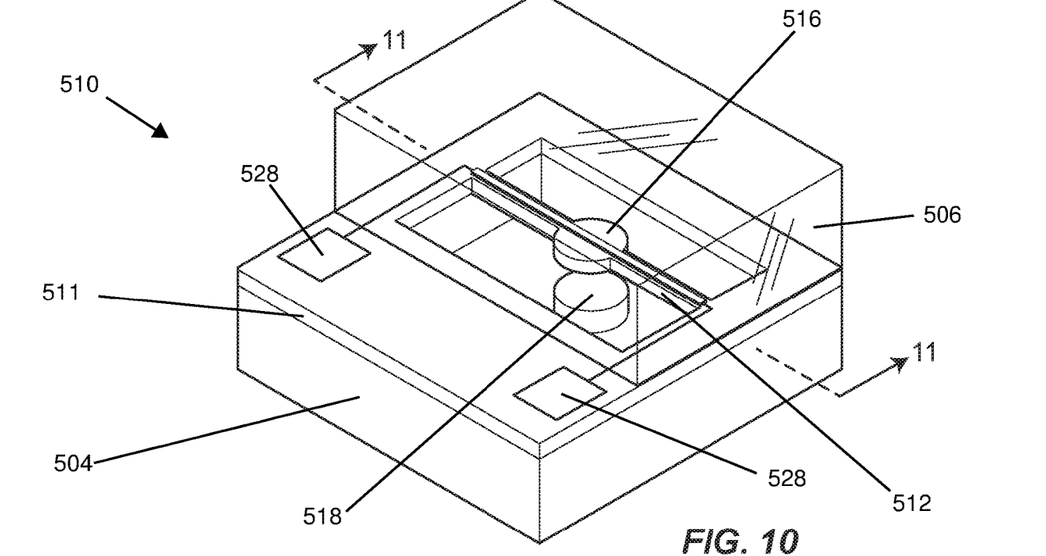
FIG. 10 is a perspective view of a Piezoresistive clot retraction assay device of an additional embodiment of the present disclosure.
Figure 11:
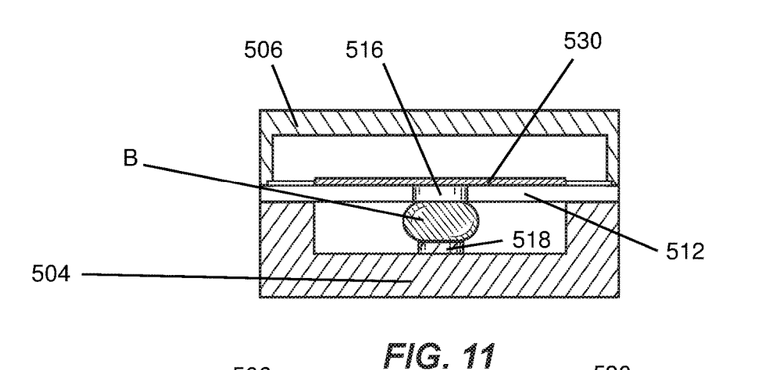
FIG. 11 is a cross-sectional view, taken along line 11-11 of FIG. 10.
Figure 12:
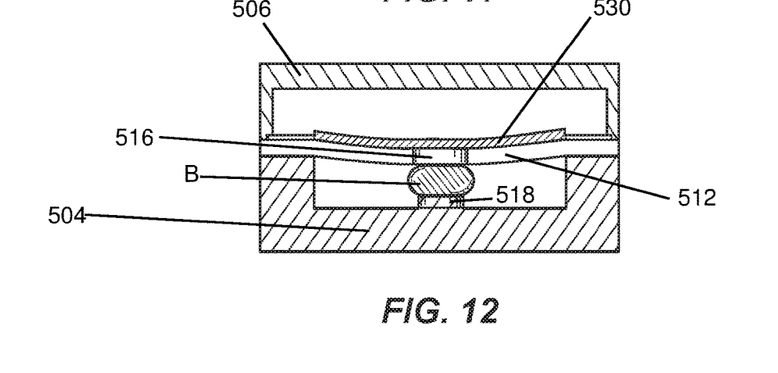
FIG. 12 is a cross-sectional view, also taken along line 11-11 of FIG. 10, but illustrating the micro-beam in a deformed condition due to coagulation of a droplet of blood received in the assay device.

In a further particular embodiment, an exemplary Piezoresistive clot retraction assay device 510 as illustrated in FIGS. 10-12 may be provided. The exemplary device 510 is configured to measure coagulation of a droplet of blood B in a manner similar to those assay devices described above, but the exemplary device 510 illustrates a Piezoresistive component 530 layered upon a micro-beam 512. Thus, the principles of operation of Piezoresistive measurement may be more clearly described. FIG. 10 illustrates a perspective view of the Piezoresistive clot assay device 510, while FIGS. 11 and 12 illustrate cross sections of the device 510 along the line 11. FIG. 11 illustrates the cross section of the device 510 when the droplet of blood B is not exerting a measurable force upon the micro-beam 512. FIG. 12 illustrates the cross section of the device 510 when the droplet of blood B is exerting a contractive force upon the micro-beam 512, such as during platelet contraction.

As illustrated, the Piezoresistive clot retraction assay device 510 has a base 504, which may have a raised plateau 518 for localizing the droplet of blood B. The base 504 and plateau 518 may be formed as one integrated component or may be joined by adhesives or other known means, and each may be made of an acrylic or other rigid material. It is desirable that the base 504 and plateau 518 should not deform in response to the contractive force exerted by the droplet of blood B, so a rigid material (or substantial qualities of a less rigid material) should be used for these components. In some embodiments, a covering 506 may be included to cover the sample area that includes the micro-beam 512. It may be beneficial to cover the sample area in order to prevent external forces from interfering with the measurement. To permit introduction of the sample droplet of blood B, the cover 506 may be removable, or a sample introduction hole (not shown) may be included.

The base 504 supports the micro-beam 512, which is illustrated as one micro-beam 512 spanning the length of the base 504. In other embodiments, multiple micro-beams 512 may be used in a manner similar to that discussed elsewhere herein. The micro-beam 512 may be made in any convenient dimensions, but a width of approximately 2 millimeters (preferably between 1 mm and 3 mm) with a height of approximately 0.3 millimeters (preferably between 0.1 mm and 0.5 mm) is preferable. In further preferred embodiments, the micro-beam 512 preferably spans a distance of approximately 15 millimeters (preferably between 10 mm and 30 mm) between the sides of the base 504. The micro-beam 512 may be made of any flexible, non-conductive material, but PDMS is particularly advantageous for its spring properties. A PDMS micro-beam 512 of the dimensions set forth above will have a spring constant of approximately 0.06 μm. As perhaps best appreciated with reference to FIG. 10, the micro-beam 512 may be formed by cutting away sections of a plate 511 in some embodiments, which plate 511 may then be attached to the base 504.

Additionally, some embodiments may include a sample platform 516 on a portion of the micro-beam 512. For example, a circular sample platform 516 having a diameter of 3 millimeters may be placed in the center of a micro-beam 512 that is 2 millimeters thick. Such sample platform 516 should align with the plateau 518 of the base 504 to localize the droplet of blood B in a particular position for measurement. The plateau 518 should be of similar (although not necessarily precisely the same) shape and area as the sample platform 516.

The Piezoresistive component 530 is attached to the micro-beam 512, such that the deformation of the micro-beam 512 due to force exerted by the droplet of blood B will cause the Piezoresistive component 530 to also deform. As illustrated, the Piezoresistive component 530 is layered upon the top of the micro-beam 512, away from the bottom side of the micro-beam 512 that will contact the droplet of blood B. The Piezoresistive component 530 may be screen-printed onto the micro-beam 512 or otherwise deposited thereon. Such screen-printed Piezoresistive component 530 may have a thickness of approximately 50 micrometers (preferably between 25 μm and 100 μm). The width of the Piezoresistive component 530 may be the full width of the micro-beam 512 or less than the full width of the micro-beam 512. For example, the Piezoresistive component 530 may be 15 mm long, 1 mm wide, and 50 μm thick. In particularly preferred embodiments, the Piezoresistive component 530 may comprise a CPDMS material, as described above. Specifically, the CPDMS material may have approximately 18% to 22% carbon concentration by weight (preferably approximately 22%). This will facilitate measurement by producing a substantial change in resistance of the Piezoresistive component 530 in response to deformation. Alternatively, the Piezoresistive component 530 may be another type of Piezoresistive material, such as other conductive polymers containing nanoscale conductive materials. For example, the Piezoresistive component 530 may be a carbon nanotube thin film deposited upon the micro-beam 512 via evaporation of the water from a carbon nanotube-in-water dispersion that contains at least water and carbon nanotubes. To facilitate electrical measurement, the Piezoresistive component 530 may be connected to electrodes 528 for further connection to an ohmmeter or multimeter (not shown). The electrodes 528 may also be screen printed on the plate 511 in some embodiments and may be made of any convenient conductive material (e.g., silver).

To measure coagulation of the droplet of blood B using the Piezoresistive clot retraction assay device 510, a resistance measurement device (e.g., an ohmmeter, not shown) is connected to the electrodes 528. The droplet of blood B is introduced to the sample area and placed between the plateau 518 and the sample platform 516. This is illustrated in FIG. 11, which shows the Piezoresistive clot retraction assay device 510 with a droplet of blood B that is not yet exerting a significant force upon the micro-beam 512. In some embodiments, an initial reading may be taken to determine the magnitude of the minimal force exerted by the droplet of blood B upon the micro-beam 512 before coagulation has begun. The droplet of blood B may be treated with a reagent to stimulate or impede coagulation, either before or after being introduced to the device 510. Alternatively, the surfaces may be coated with various agonists or antagonists of the cellular or acellular components of coagulation in order to identify the particular coagulation defect. As coagulation proceeds, the droplet of blood B will contract, which will exert a force upon the sample platform 516 and the plateau 518. Because the plateau 518 and base 504 are rigid relative to the micro-beam 512, the sample platform 516 of the micro-beam 512 will be pulled toward the plateau 518 by this contractive force. The Piezoresistive component 530 will likewise be pulled toward the plateau 518 by the micro-beam 512. The resulting deformation of the micro-beam 512 and the Piezoresistive component 530 is shown in FIG. 12. As the Piezoresistive component 530 deforms in response to the contractive force of the droplet of blood B, the length of the Piezoresistive component 530 increases and part of the Piezoresistive component 530 become thinner. This deformation changes the geometry of the Piezoresistive component 530, which results in a change in resistance of the Piezoresistive component 530. The change in resistance may be measured in real time (either periodically or continuously) as the droplet of blood B coagulates.

From the readings of the changes in resistance of the Piezoresistive component 530, information regarding the extent and timing of coagulation may be determined and analyzed to further determine a blood coagulation profile or characteristics of the patient from whom the sample was taken. Because the amount of blood required for each sample is so small (approximately 15 µL), multiple Piezoresistive clot retraction assay devices 510 may be used to simultaneously test the responses of the blood to different types or quantities of pro- or anti-coagulants. Thus, a fuller picture of the coagulation response of a patient may be obtained in real time with very little blood drawn. This is particularly important for pediatric, neonatal, or other patients for whom drawing large quantities of blood for testing would be dangerous or impractical.

As noted above, the mHRM 10 may be divided into two distinct parts: a removable cartridge that receives the droplet of blood B and a receiving unit that receives cartridges and performs measurements. Such embodiments are advantageous inasmuch as they separate the electronic and computing components (e.g., an ohmmeter for measuring resistance across the Piezoresistive components and a processor for determining force based upon changes in measured resistance) from the measurement structure (e.g., the micro-beams and base to which the droplet of blood B adheres). Because the electronic and computing components are relatively more durable and expensive than the measurement structure, the receiving unit may be used to measure coagulation of many blood samples. In contrast, the measurement structure must be cleaned between each sample, which may be time-consuming and may degrade the measurement accuracy over time. Because the components of the measurement structure can be manufactured relatively easily and cheaply, the measurement structure may be separated into a removable cartridge. In some embodiments, such cartridges may be configured to receive the droplet of blood B prior to insertion of the cartridge into the receiving unit.

As an example, the device 510 may be a removable cartridge in some such embodiments. Such cartridge may connect to a measurement device within the receiving unit by an electrical connection to the electrodes 528 when the cartridge is inserted within the receiving unit. The measurement device may be an ohmmeter, multimeter, or other similar devices, as described elsewhere herein. In operation, the droplet of blood B may be introduced into the sample area between the plateau 518 and the sample platform 516 prior to insertion of the cartridge into the receiving unit. The covering 506 may then be moved into place to avoid contamination of the receiving unit by any portion of the blood sample to be assessed. The cartridge (the device 510) may then be inserted into the receiving unit (not shown). A chemical or other means of inducing coagulation may be introduced, either before or after the cartridge is inserted within the receiving unit. Following insertion of the cartridge, a measurement device of the receiving unit may begin measurement of the resistance across the Piezoresistive component 530 via the connections with the electrodes 528. In some embodiments, a plurality of resistance measurements may be taken to determine various metrics associate with the blood sample, as described further below. The measurement device may further be communicatively connected to a processing component of receiving unit, which may determine the various metrics based upon resistance measurements received from the measurement device, as described further below.

Figure 13:
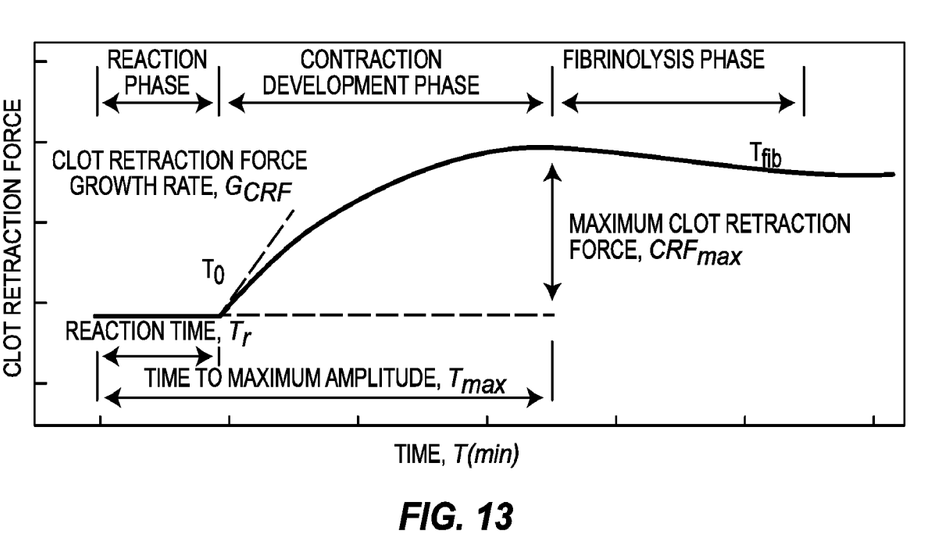
FIG. 13 is a chart illustrating clot retraction force during coagulation.

FIG. 13 illustrates change in blood clot retraction force over time during coagulation. The clotting process may be divided into three phases, as shown. First, a reaction phase exists from the time clotting is induced ($T_0$) until the onset of clot development ($T_r$), indicating a reaction time. Second, a contraction development phase exists from the onset of clot development at the reaction time ($T_r$) until the maximum clot retraction force is reached ($T_{max}$). Third, a fibrinolysis phase exists from the time the maximum clot retraction force is reached ($T_{max}$) until the time a steady-state plateau is reached ($T_{fib}$). Thus, the chart of FIG. 13 illustrates the changes of the clot retractive force of a whole blood sample over these three phases. The various embodiments of the measurement devices described above facilitate measurement of metrics associated with the phases, may be used to determine important aspects of hemostasis under different clotting agent and pro- and anti-coagulant treatments. Such metrics may include absolute or relative durations of each phase, magnitudes of clot retraction forces, or changes in magnitudes of clot retraction forces.

During the reaction phase, the coagulation cascade is underway for formation of the fibrin network needed for clot retraction force development. While this occurs, no discernible change to the clot retraction force is observed, viz. the clot retraction force remains at zero or a negligible value. Once the fibrin network is in place, the onset of clot retraction force development is observed, identifying the beginning of the contraction development phase. During the contraction development phase, interactions between activated platelets and fibrin strands lead to a rapid increase of clot retraction force and initiation of blood clot contraction. A growth rate of clot retraction force ($G_{CRF}$) may be measured as the rate of change of the clot retraction force at the reaction time ($T_r$), which may also be defined as the first derivative of clot retraction force with respect to time at the reaction time. Although the growth rate of clot retraction force ($G_{CRF}$) at the reaction time ($T_r$) is a particularly useful metric, other growth rates may be measured at other times during the contraction phase or fibrinolysis phase. The clot retraction force continues to increase during the contraction development phase, until the maximum clot retraction force ($CRF_{max}$) is reached, which value is also a particularly useful metric. Once the maximum clot retraction force ($CRF_{max}$) is reached, the fibrinolysis phase begins, during which clot retraction force decreases slowly from the maximum clot retraction force to a plateau or steady-state value of the clot retraction force as the fibrin network disintegrates. In some embodiments, various metrics described above may be measured using clot retraction devices as described herein. Additionally, some embodiments may include one or more generated charts or plots, such as the chart illustrated in FIG. 13.

Aside from measurement and diagnostic purposes, the process described above would normally occur within a patient's body. It would thus be subject to variable conditions that can, in some instances, exert considerable influence upon the results. Two such conditions of particular interest are temperature within the patient's body and sheer forces from blood circulation. In some embodiments, therefore, the devices and methods described herein may be modified to control these conditions. In some such embodiments, temperature may be measured for the sample area where the droplet of blood B is placed for retractive force measurement, such as by thermocouples or digital thermometers. In further embodiments, heating or cooling elements may be included to control the temperature of the sample area. In additional embodiments, sheer forces caused by blood circulation may be mimicked by introducing vibrations to the measurement device. In some such embodiments, the sample area may be disposed within a hollow tube or sphere, configured to resemble a vein or artery. A vibrating element, such as a micromechanical vibrating motor, may be added to the device to generate sheer forces. Such vibrating element may be controlled to operate continuously or at intervals mimicking the flow of blood in response to a heartbeat. Alternatively, the sample area or the entire clot retraction assay device may be disposed within a fluidic channel supplied by a controllable fluid source. A fluid may thus be introduced to exert a controllable sheer stress on the droplet of blood B, thereby mimicking the sheer forces from blood circulation within a patient's circulatory system. Such temperature and/or sheer force conditions may be used, in some embodiments, to initiate clotting in response to these conditions.

As described herein, various devices and methods for measuring retractive forces exerted by blood clots and for using such measurements are disclosed. As discussed above, such forces are measured indirectly through their effects on deformation and displacement of micro-beams. Direct measurements of the displacement of the micro-beams may be optical, Piezoresistive, or by other techniques. When optical, image data may be automatically processed to determine the force associated with micro-beam displacement or deformation. When Piezoresistive, resistance measurements may be automatically processed to determine corresponding force, also based upon micro-beam displacement or deformation (as measured through a change in resistance). One or more processing components may be used to perform such processing and determine the corresponding retractive forces. The processing components may include one or more general-purpose computer processors configured by executable instructions to perform such processing, or the processing components may include one or more special-purpose processors permanently configured to perform such processing. The processing components may similarly include field programmable gate arrays or other similar components. The processing components may be disposed within the clot retraction assay devices described herein or may be communicatively connected thereto, such as via a wired or wireless communication connection. In some embodiments, a general-purpose computer may be connected to the clot retraction assay device to process measurements of resistance caused by (or images showing) micro-beam displacement or deformation.

While various embodiments have been described herein, it will be understood that variations may be made thereto that are still within the scope of the appended claims.

What is claimed is:

1. A clot retraction assay device for assessing a blood sample, comprising:
   a micro-beam made of a deformable material, having at least one end connected to a support and extending away from the support in an axial direction;
   a Piezoresistive component disposed upon a surface of the micro-beam along the axial direction; and
   a resistance measurement device connected to a plurality of points of the Piezoresistive component, the points separated by a distance in the axial direction,
   wherein the resistance measurement device is configured to measure a change in resistance across a portion of the Piezoresistive component resulting from deformation in response to a retractive force exerted upon the micro-beam by the blood sample, and
   wherein the Piezoresistive component comprises a carbon-polydimethylsiloxane (CPDMS) composite.

2. The clot retraction assay device of claim 1, wherein the CPDMS composite is between 10% and 26% carbon by weight.

3. A clot retraction assay device for assessing a blood sample, comprising:
   a micro-beam made of a deformable material, having at least one end connected to a support and extending away from the support in an axial direction;
   a Piezoresistive component disposed upon a surface of the micro-beam along the axial direction; and
   a resistance measurement device connected to a plurality of points of the Piezoresistive component, the points separated by a distance in the axial direction,
   wherein the resistance measurement device is configured to measure a change in resistance across a portion of the Piezoresistive component resulting from deformation in response to a retractive force exerted upon the micro-beam by the blood sample, and wherein:

two ends of the micro-beam are connected to the support;

the micro-beam is integrated into the support as a portion of one sheet of material;

the Piezoresistive component extends between the two ends of the micro-beam; and the resistance measurement device is connected to the Piezoresistive component at each of the two ends of the micro-beam.

4. A clot retraction assay device for assessing a blood sample, comprising:

a micro-beam made of a deformable material, having at least one end connected to a support and extending away from the support in an axial direction;

a Piezoresistive component disposed upon a surface of the micro-beam along the axial direction;

a resistance measurement device connected to a plurality of points of the Piezoresistive component, the points separated by a distance in the axial direction, wherein the resistance measurement device is configured to measure a change in resistance across a portion of the Piezoresistive component resulting from deformation in response to a retractive force exerted upon the micro-beam by the blood sample, further comprising a rigid base connected to the micro-beam, either directly or through the support, wherein:

the micro-beam includes a platform area having a platform width greater than a beam width of the micro-beam in a direction normal to the axial direction;

the platform area is located a separation distance from a sample plateau of rigid base; and the size of each of the platform area and the sample plateau and the separation distance are configured to hold the blood sample between the platform area and the sample plateau by non-specific adhesion resulting from surface tension, the blood sample having a volume between 15 microliters and 300 microliters.

5. A clot retraction assay device for assessing a blood sample, comprising:

a micro-beam made of a deformable material, having at least one end connected to a support and extending away from the support in an axial direction;

a Piezoresistive component disposed upon a surface of the micro-beam along the axial direction; and a resistance measurement device connected to a plurality of points of the Piezoresistive component, the points separated by a distance in the axial direction, wherein the resistance measurement device is configured to measure a change in resistance across a portion of the Piezoresistive component resulting from deformation in response to a retractive force exerted upon the micro-beam by the blood sample, and wherein the micro-beam and Piezoresistive component are disposed within a removable cartridge, and further comprising a receiving unit configured to receive the cartridge, the receiving unit comprising:

the resistance measurement device;

a plurality of conductive connections to the cartridge, wherein the conductive connections form conductive connections between the resistance measuring device and the plurality of points of the Piezoresistive component;

a processing component communicatively connected to an output of the resistance measurement device, wherein the processing component is configured to determine the retractive force exerted by the blood sample based upon the measured change in resistance across the portion of the Piezoresistive component.

* * * * *